United States Patent
Hsu et al.

(10) Patent No.: US 7,935,837 B2
(45) Date of Patent: May 3, 2011

(54) PROCESS FOR SYNTHESIS OF ANDROSTANE 17-β CARBOTHIOIC ACID AND RELATIVE COMPOUNDS THEREOF

(75) Inventors: Nai-Hsuan Hsu, Taipei (TW); Chu-Yi Pang, Taipei (TW); Chien-Jen Wu, Taipei (TW); Chi-Jen Huang, Taipei (TW); Chia-Jung Hsu, Taipei (TW); Peimin Lee, Taipei (TW)

(73) Assignee: Corum Inc., Taipei (TW)

( * ) Notice: Subject to any disclaimer, the term of this patent is extended or adjusted under 35 U.S.C. 154(b) by 587 days.

(21) Appl. No.: 12/112,229

(22) Filed: Apr. 30, 2008

(65) Prior Publication Data
US 2009/0275767 A1 Nov. 5, 2009

(51) Int. Cl.
*C07J 3/00* (2006.01)

(52) U.S. Cl. .................................................... 552/610

(58) Field of Classification Search ................... 552/610
See application file for complete search history.

(56) References Cited

U.S. PATENT DOCUMENTS

| | | | |
|---|---|---|---|
| 2,568,020 A * | 9/1951 | McCool | 562/26 |
| 3,086,049 A * | 4/1963 | Godfrey | 564/215 |
| 4,335,121 A | 6/1982 | Phillipps et al. | |
| 4,650,610 A | 3/1987 | Phillipps et al. | |

FOREIGN PATENT DOCUMENTS

WO    WO03/037855 A1 *  5/2003

\* cited by examiner

*Primary Examiner* — Barbara P Badio
(74) *Attorney, Agent, or Firm* — WPAT, PC; Justin King

(57) ABSTRACT

A process for synthesis of androstane 17-β carbothioic acid is provided. The process includes mixing an androstane 17-β carboxylic acid and a coupling reagent, and adding an alkanethioic acid to form an androstane 17-β carbothioic acid, wherein the androstane 17-β carbothioic acid has the formula (I):

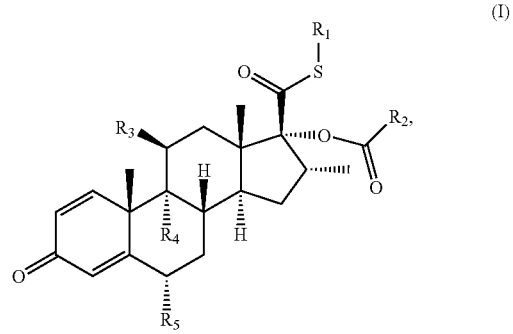

wherein $R_1$ represents hydrogen or haloalkyl groups, $R_2$ represents $C_{1-8}$ linear alkyl groups, $C_{1-8}$ branched alkyl groups, $C_{1-6}$ unsaturated acyclic groups or aromatic groups, $R_3$ represents hydrogen or hydroxyl, $R_4$ represents hydrogen, bromine, chlorine or fluorine and $R_5$ represents hydrogen, bromine, chlorine or fluorine. The process is a one-pot reaction.

7 Claims, No Drawings

PROCESS FOR SYNTHESIS OF ANDROSTANE 17-β CARBOTHIOIC ACID AND RELATIVE COMPOUNDS THEREOF

BACKGROUND OF THE INVENTION

1. Field of the Invention

The invention relates to a preparation of androstane 17-β carbothioic acid and relative compounds thereof, and in particular, to a preparation of androstane 17-β carbothioic acid without addition of hydrogen sulphide.

2. Description of the Related Art

Androstane compounds containing a carbothioate group in the 17β position have been found to possess anti-inflammatory properties. In particular such androstane compounds are disclosed in U.S. Pat. No. 4,650,610 filed by G. H. Philipps, B. M. Bain, C. Williamson, I. P. Steeples and S. B. Laing and U.S. Pat. No. 4,335,121 filed by G. H. Philipps.

However, the addition of a gaseous hydrogen sulphide, a toxic substance, is required for the conventional androstane preparation process, seriously affecting fabrication safety. Also, three or four preparation steps are required, making the preparation costly.

BRIEF SUMMARY OF THE INVENTION

One embodiment of the invention provides a process for synthesis of androstane 17-β carbothioic acid comprising mixing an androstane 17-β carboxylic acid and a coupling reagent, and adding an alkanethioic acid to form an androstane 17-β carbothioic acid, wherein the androstane 17-β carbothioic acid has the formula (I):

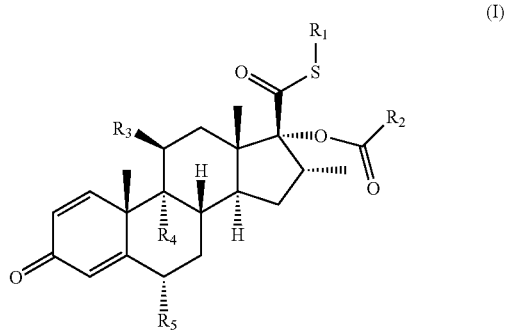

(I)

wherein $R_1$ represents hydrogen or haloalkyl groups, $R_2$ represents $C_{1-8}$ linear alkyl groups, $C_{1-8}$ branched alkyl groups, $C_{1-6}$ unsaturated acyclic groups or aromatic groups, $R_3$ represents hydrogen or hydroxyl, $R_4$ represents hydrogen, bromine, chlorine or fluorine and $R_5$ represents hydrogen, bromine, chlorine or fluorine In an embodiment of the invention, alkanethioic acid is substituted for the conventional toxic hydrogen sulphide, improving preparation safety and reducing preparation steps. Compared with conventional gaseous hydrogen sulphide, by using the alkanethioic acid, the equivalent of reactants of the invention is more accurately determined. Additionally, after addition of the alkanethioic acid, an intramolecular rearrangement in the thio-anhydride intermediate occurs, facilitating preparation.

A detailed description is given in the following embodiments.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

One embodiment of the invention provides a process for synthesis of androstane 17-β carbothioic acid. The process is disclosed in the following scheme. First, an androstane 17-β carboxylic acid (compound I) and a coupling reagent are mixed to form a compound II (step a). The coupling reagent may comprise N,N'-carbonyldiimidazole, N,N'-carbonyldi(1,2,4-triazole), N,N'-carbonylbenzotriazole, N,N'-carbonylbenzimidazole, N,N'-carbonyldi(3,5-dimethylpyrazole), N,N'-thiodiimidazole, N,N'-carbonyldiimidazole, N,N'-thiocarbonyldiimidazole, N,N'-Dicyclohexylcarbodiimide/N-Hydroxysuccinimide (DCC/HOSu), N,N'-Dicyclohexylcarbodiimide/N-Hydroxybenzotriazole (DCC/HOBt), N,N'-Diisopropylcarbodiimide/N-Hydroxysuccinimide (DIC/HOSu) or N,N'-Diisopropylcarbodiimide/N-Hydroxybenzotriazole (DIC/HOBt). Next, an alkanethioic acid is added to form a thio-anhydride (compound III) (step b). The alkanethioic acid may have a formula such as

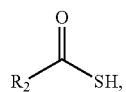

wherein $R_2$ may comprise $C_{1-8}$ linear alkyl groups, $C_{1-8}$ branched alkyl groups, $C_{1-6}$ unsaturated acyclic groups or aromatic groups, for example, propanethioic acid, ethanethioic acid or thiobenzoic acid. The thio-anhydride (compound III) is intramolecularly rearranged to form an androstane 17-β carbothioic acid (compound IV) (step c). The androstane 17-β carbothioic acid (compound IV) is then esterified by, for example, addition of a dihaloalkane such as bromochloromethane, fluoroiodomethane, iodochloromethane or bromofluoromethane, to prepare an androstane 17-β carbothioate (compound V) (step d). Specifically, the process is a one-pot reaction without purification steps.

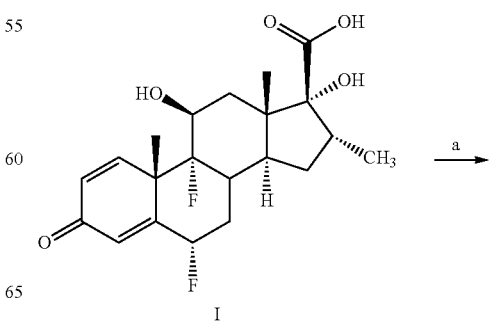

I

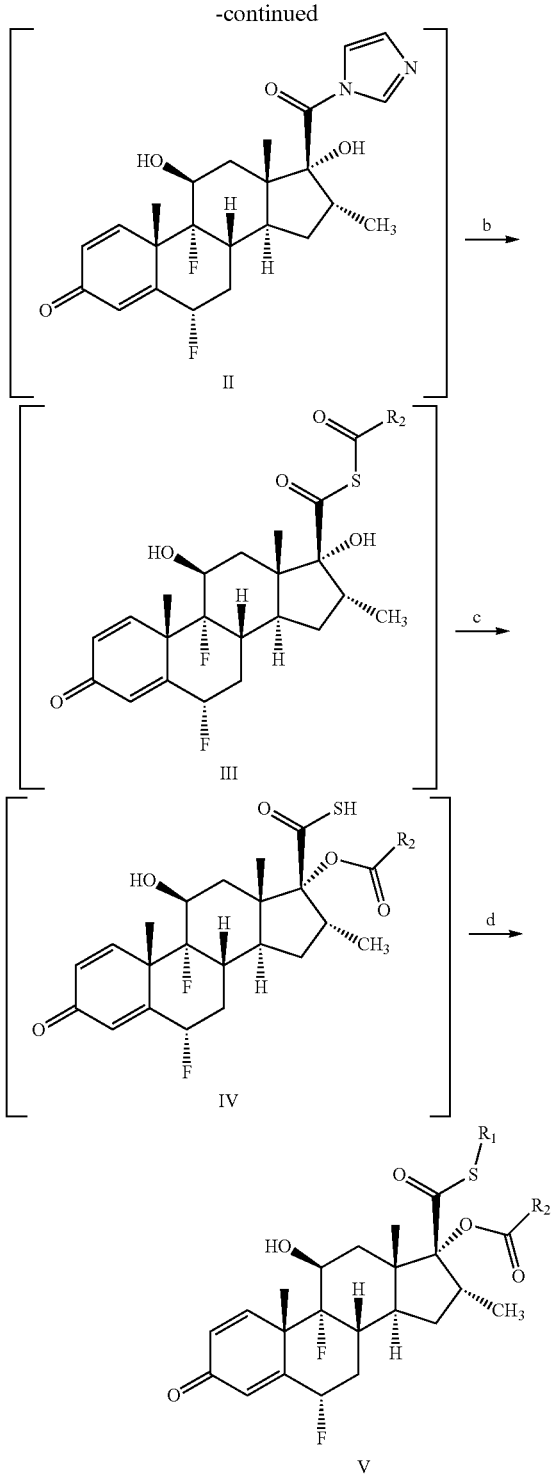

Example 1

Preparation of Propanethioic Acid

Hydrogen sulfide was passed into a solution of 120 mL propionic anhydride (129 g, 1.074 mol) containing 1.74 g sodium hydroxide (0.043 mol) as rapidly as possible. The temperature of the solution was risen to 55° C. within 30 minutes and kept at 50-55° C. by water bath cooling. After a total reaction period of 6 hours, the gain in weight of the reaction mixture was about 27 g. The reaction mixture was distilled rapidly at 130 torr to separate sodium salt. The mixture of thiopropionic acid and propionic acid were fractionally distilled again. The distillate of thiopropionic acid boiling in 130 torr at 30-33° C. was 57.0 mL.

Example 2

Preparation of 6α,9-Difluoro-11β-hydroxy-16α-methyl-3-oxo-17α-benzoyl-oxyandrosta-1,4-diene-17β-carbothioic acid

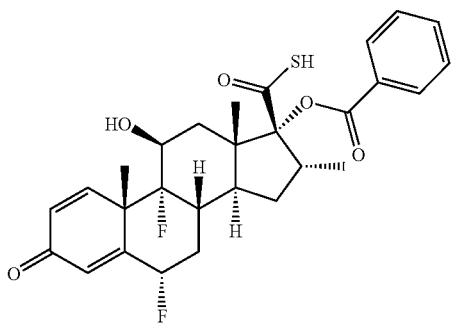

A stirred solution of 60 mL dry tetrahydrofuran containing 1.503 g 6α,9-Difluoro-11β,17α-Dihydroxy-16α-methyl-3-oxyandrosta-1,4-diene-17β-carboxylic acid was cooled at 5° C. under nitrogen and treated with 1.537 g N,N'-carbonyldiimidazole, with stirring at 5° C. for 18 hrs. 5.240 g thiobenzoic acid was dropped into the reaction for 1 hr and the solution was stirred for a further 6 hrs, gradually being allowed to warm to 25° C. The reaction was diluted with 60 mL ethyl acetate, and washed with 6 mL hydrochloric acid (1N) and water (2×60 mL) to pH 7. The organic layer was extracted with 5% sodium bicarbonate solution (2×60 mL). The water layer was then treated with 2.604 mL hydrochloric acid (1N) to neutralize. The reaction was extracted with 60 mL ethyl acetate and vacuum concentrated at 45° C. to dry, to result in 0.881 g carbothioic acid.

Example 3

Preparation of 6,9-Difluoro-11-hydroxy-16-methyl-3-oxo-17-acetyl-oxyandrosta-1,4-diene-17-carbothioic acid

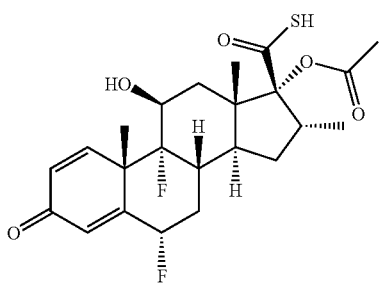

In an embodiment of the invention, the conventional toxic hydrogen sulphide is replaced by alkanethioic acid, improving preparation safety and reducing preparation steps. Compared with conventional gaseous hydrogen sulphide, by using the alkanethioic acid, the equivalent of reactants of the invention is more accurately determined. Additionally, after addition of the alkanethioic acid, an intramolecular rearrangement in the thio-anhydride intermediate occurs, facilitating preparation.

A stirred solution of 60.7 mL dry acetonitrile containing 1.501 g 6□,9-Difluoro-11□,17□-Dihydroxy-16□-methyl-3-oxyandrosta-1,4-diene-17□-carboxylic acid was cooled at 5° C. under nitrogen and treated with 1.535 g N,N'-carbonyldiimidazole, with stirring at 5° C. for 18 hrs. 2.882 g thioacetic acid was dropped into the reaction for 1 hr and the solution was stirred for a further 6 hrs, gradually being allowed to warm to 25° C. The reaction was diluted with 60 mL ethyl acetate, and washed with 6 mL hydrochloric acid (1N) and water (2×60 mL) to pH 7. The organic layer was extracted with 5% sodium bicarbonate solution (2×60 mL). The water layer was then treated with 2.598 mL hydrochloric acid (1N) to neutralize. The reaction was extracted with 60 mL ethyl acetate and vacuum concentrated at 45° C. to dry, to result in 1.231 g carbothioic acid.

Example 4

Preparation of 6α,9-Difluoro-11β-hydroxy-16α-methyl-3-oxo-17α-propionyl-oxyandrosta-1,4-diene-17β-carbothioic acid

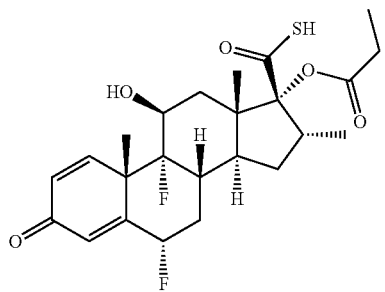

A stirred solution of 85.4 mL dry tetrahydrofuran containing 2.112 g 6α,9-Difluoro-11β,17α-Dihydroxy-16α-methyl-3-oxyandrosta-1,4-diene-17β-carboxylic acid was cooled at 5□ under nitrogen and treated with 2.160 g N,N'-carbonyldiimidazole, with stirring at 5° C. for 18 hrs. 4.802 g propanethioic acid was dropped into the reaction for 1 hr and the solution was stirred for a further 6 hrs, gradually being allowed to warm to 25° C. The reaction was diluted with 50 mL ethyl acetate, and washed with 10 mL hydrochloric acid (1N) and water (2×50 mL) to pH 7. The organic layer was extracted with 5% sodium bicarbonate solution (2×50 mL). The water layer was then treated with 2.17 mL hydrochloric acid (1N) to neutralize. The reaction was extracted with 50 mL ethyl acetate and vacuum concentrated at 45° C. to dry, to result in 1.102 g carbothioic acid.

Example 5

Preparation of 6α,9-Difluoro-11β-hydroxy-16α-methyl-3-oxo-17α-propionyl-oxyandrosta-1,4-diene-17β-carbothioic acid

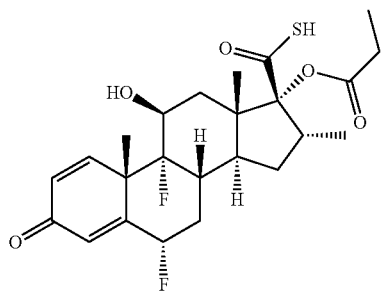

A stirred solution of 102.5 mL N-Methylpyrrolidone containing 2.534 g 6α,9-Difluoro-11β,17α-Dihydroxy-16α-methyl-3-oxyandrosta-1,4-diene-17β-carboxylic acid was cooled at 5° C. under nitrogen and treated with 2.592 g N,N'-carbonyldiimidazole, with stirring at 5° C. for 18 hrs. 5.762 g propanethioic acid was dropped into the reaction for 1 hr and the solution was stirred for a further 6 hrs, gradually being allowed to warm to 25° C. The reaction was diluted with 60 mL ethyl acetate, and washed with 6 mL hydrochloric acid (1N) and water (2×60 mL) to pH 7. The organic layer was extracted with 5% sodium bicarbonate solution (2×60 mL). The water layer was then treated with 2.604 mL hydrochloric acid (1N) to neutralize. The reaction was extracted with 60 mL ethyl acetate and vacuum concentrated at 45° C. to dry, to result in 1.212 g carbothioic acid.

Example 6

Preparation of 6α,9-Difluoro-11βhydroxy-16α-methyl-3-oxo-17α-propionyloxyandrosta-1,4-diene-17β-carbothioic acid

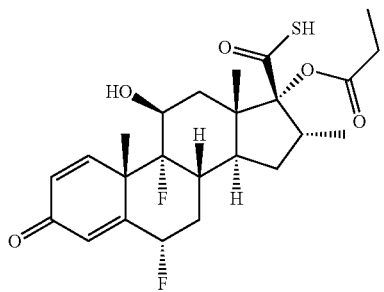

A stirred solution of 74.1 mL dry acetonitrile containing 1.831 g 6α,9-Difluoro-11β,17α-Dihydroxy-16α-methyl-3-oxyandrosta-1,4-diene-17β-carboxylic acid was cooled at 5° C. under nitrogen and treated with 1.872 g N,N'-carbonyldiimidazole, with stirring at 5° C. for 18 hrs. 0.416 g propanethioic acid was dropped into the reaction for 1 hr and the solution was stirred for a further 6 hrs, gradually being allowed to warm to 25° C. The reaction was diluted with 70 mL ethyl acetate, and washed with 7 mL hydrochloric acid (1N) and water (2×70 mL) to pH 7. The reaction was extracted with 70 mL ethyl acetate and vacuum concentrated at 45° C. to dry, to result in 1.623 g carbothioic acid.

Example 7

Preparation of S-Chloromethyl 6α,9-Difluoro-11β-hydroxy-16α-methyl-3-oxo-17α-propionyloxyandrosta-1,4-diene-17β-carbothioate

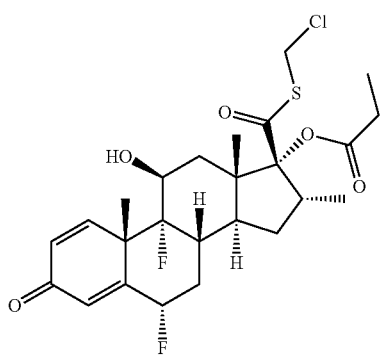

A stirred solution of 40 mL dry acetonitrile containing 1.313 g 6α,9α-Difluoro-11β-hydroxy-16α-methyl-3-oxo-17α-propionyloxyandrosta-1,4-diene-17β-carbothioic acid (from example 5) was cooled at 5° C. 4.714 g Sodium bicarbonate was added to the reaction and stirred for 30 min. 9.4 mL bromochloromethane was then treated into the reaction and stirred for a further 12 hrs, gradually being allowed to warm to 25° C. The reaction was washed with 20% sodium chloride solution (2×55 mL). The reaction was vacuum concentrated to slurry then treated with 8.9 mL isopropyl alcohol, and concentrated at 45° C. to slurry. The residue was filtrated and washed with 2.2 mL isopropyl alcohol to result in 1.204 g S-chloromethyl ester.

Example 8

Preparation of S-Chloromethyl 6α,9-Difluoro-11β-hydroxy-16α-methyl-3-oxo-17α-propionyloxyandrosta-1,4-diene-17β-carbothioate

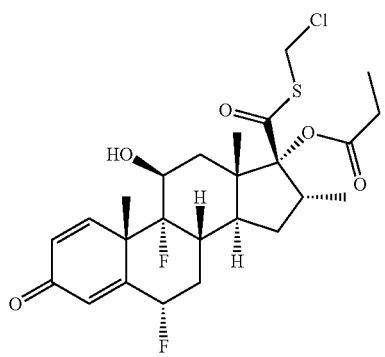

A stirred solution of 40.9 mL dry acetonitrile containing 1.011 g 6α,9-Difluoro-11β,17α-Dihydroxy-16α-methyl-3-oxyandrosta-1,4-diene-17β-carboxylic acid was cooled at 5° C. under nitrogen and treated with 1.034 g N,N'-carbonyldiimidazole, with stirring at 5° C. for 18 hrs. 2.299 g propanethioic acid was dropped into the reaction for 1 hr and the solution was stirred for a further 6 hrs. 4.285 g Sodium bicarbonate was added to the reaction and stirred for 30 min. 8.5 mL bromochloromethane was then treated into the reaction and stirred for a further 12 hrs, gradually being allowed to warm to 25° C. The reaction was washed with 20% sodium chloride solution (2×50 mL). The reaction was vacuum concentrated to slurry then treated with 8.0 mL isopropyl alcohol, and concentrated at 45° C. to slurry. The residue was filtrated and washed with 2.0 mL isopropyl alcohol to result in 1.055 g S-chloromethyl ester.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A process for synthesis of androstane 17-β carbothioic acid, comprising:
   mixing an androstane 17-β carboxylic acid and a coupling reagent; and
   adding an alkanethioic acid to form an androstane 17-β carbothioic acid, wherein the androstane 17-β carbothioic acid has the formula (I):

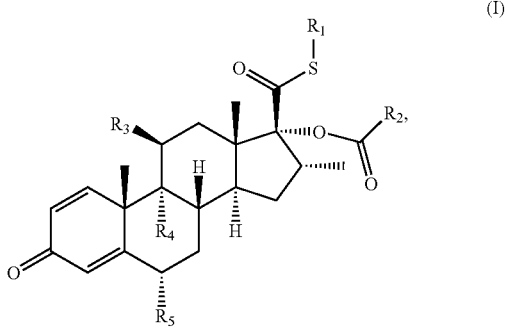

wherein $R_1$ represents hydrogen or haloalkyl groups, $R_2$ represents $C_{1-8}$ linear alkyl groups, $C_{1-8}$ branched alkyl groups, $C_{1-6}$ unsaturated acyclic groups or aromatic groups, $R_3$ represents hydrogen or hydroxyl, $R_4$ represents hydrogen, bromine, chlorine or fluorine and $R_5$ represents hydrogen, bromine, chlorine or fluorine.

2. The process according to claim 1, wherein the coupling reagent is selected from N,N'-carbonyldiimidazole, N,N'-carbonyldi(1,2,4-triazole), N,N'-carbonylbenzotriazole, N,N'-carbonylbenzimidazole, N,N'-carbonyldi(3,5-dimethylpyrazole), N,N'-thiodiimidazole, N,N'-carbonyldiimidazole, N,N'-thiocarbonyldiimidazole, N,N'-Dicyclohexylcarbodiimide/N-Hydroxysuccinimide (DCC/HOSu), N,N'-Dicyclohexylcarbodiimide/N-Hydroxybenzotriazole (DCC/HOBt), N,N'-Diisopropylcarbodiimide/N-Hydroxysuccinimide (DIC/HOSu) or N,N'-Diisopropylcarbodiimide/N-Hydroxybenzotriazole (DIC/HOBt).

3. The process according to claim 1, wherein the alkanethioic acid has the formula (II):

wherein $R_2$ represents $C_{1-8}$ linear alkyl groups, $C_{1-8}$ branched alkyl groups, $C_{1-6}$ unsaturated acyclic groups or aromatic groups.

4. The process according to claim 3, wherein the alkanethioic acid is selected from propanethioic acid, ethanethioic acid or thiobenzoic acid.

5. The process according to claim 1, wherein the androstane 17-β carbothioic acid is further esterified by adding a dihaloalkane.

6. The process according to claim 5, wherein the dihaloalkane is selected from bromochloromethane, fluoroiodomethane, chloroiodomethane or bromofluoromethane.

7. The process according to claim 1, wherein the process for synthesis of androstane 17-β carbothioic acid is a one-pot reaction.

* * * * *